United States Patent
Kasielke et al.

(10) Patent No.: US 7,638,033 B2
(45) Date of Patent: Dec. 29, 2009

(54) BIOSENSOR SYSTEM

(75) Inventors: Joachim Kasielke, Brühl (DE); Michael Marquant, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1027 days.

(21) Appl. No.: 11/246,381

(22) Filed: Oct. 7, 2005

(65) Prior Publication Data

US 2006/0108236 A1    May 25, 2006

Related U.S. Application Data

(63) Continuation of application No. PCT/EP2004/002646, filed on Mar. 13, 2004.

(30) Foreign Application Priority Data

Apr. 8, 2003    (EP) .................................. 03008143

(51) Int. Cl.
    *G01N 27/327*    (2006.01)
(52) U.S. Cl. .................. 205/775; 205/777.5; 204/403.1
(58) Field of Classification Search ...............................
    204/403.01–403.15, 400, 416–419; 205/775, 205/777.5, 778, 792
    See application file for complete search history.

(56) References Cited

U.S. PATENT DOCUMENTS

| | | | |
|---|---|---|---|
| 4,005,002 A * | 1/1977 | Racine et al. ............ | 204/403.1 |
| 4,919,770 A | 4/1990 | Preidel et al. | |
| 5,243,516 A | 9/1993 | White | |
| 6,413,411 B1 | 7/2002 | Pottgen et al. | |

(Continued)

FOREIGN PATENT DOCUMENTS

WO    WO 99/18430    4/1999

(Continued)

OTHER PUBLICATIONS

Zuping Tang et al., Éffects of Different Hematocrit Levels on Glucose Measurements With Handheld Meters for Point-of-Care Testing, *Arch Pathol Lab Med*, vol. 124, pp. 1135-1140, (2000).

(Continued)

*Primary Examiner*—Alex Noguerola
(74) *Attorney, Agent, or Firm*—Justin L. Sage; Roche Diagnostics Operations, Inc.

(57) ABSTRACT

Biosensor system and method for the electrochemical determination of an concentration of an analyte in a sample. An analyte reactant is at least partially hydrated by the sample to form a reaction layer in contact with electrodes for measurement of an analyte detection current. The analyte detection current is characteristic of the analyte concentration in the sample by virtue of a reaction sequence comprising an analyte-specific reaction taking place in the reaction layer and an electrode reaction including transfer of electrons through an electrode surface. A plurality of values of a curve of the analyte detection current versus time are measured and the analyte concentration is derived therefrom by means of an evaluation algorithm. Fast results of high accuracy are achieved in that the DC-voltage is applied to the electrodes during the analyte-specific reaction whereby the analyte-specific reaction and the electrode reaction take place generally simultaneously resulting in an analyte detection current versus time curve which comprises a rising section in which the current increases versus time and the analyte detection current is measured at at least two points of time in the rising section and the values of the analyte detection current resulting from said at least two measurements are used in the evaluation algorithm for error compensation.

46 Claims, 7 Drawing Sheets

U.S. PATENT DOCUMENTS 6,475,360 B1 * 11/2002 Hodges et al. ......... 204/403.14
2004/0154932 A1 * 8/2004 Deng et al. .............. 205/777.5

FOREIGN PATENT DOCUMENTS

| WO | WO 99/32881 | 7/1999 |
| WO | WO 99/46585 | 9/1999 |
| WO | WO 01/88534 A2 | 11/2001 |

OTHER PUBLICATIONS

XP004004390—Petr Skladal, "Compensation of Temperature Variations Disturbing Performance of an Amperometric Biosensor for Continuous Monitoring," *Sensors and Actuators B 28*, pp. 59-62, (1995).

* cited by examiner

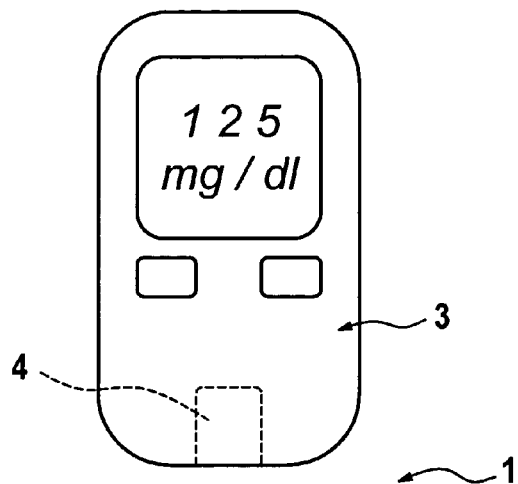
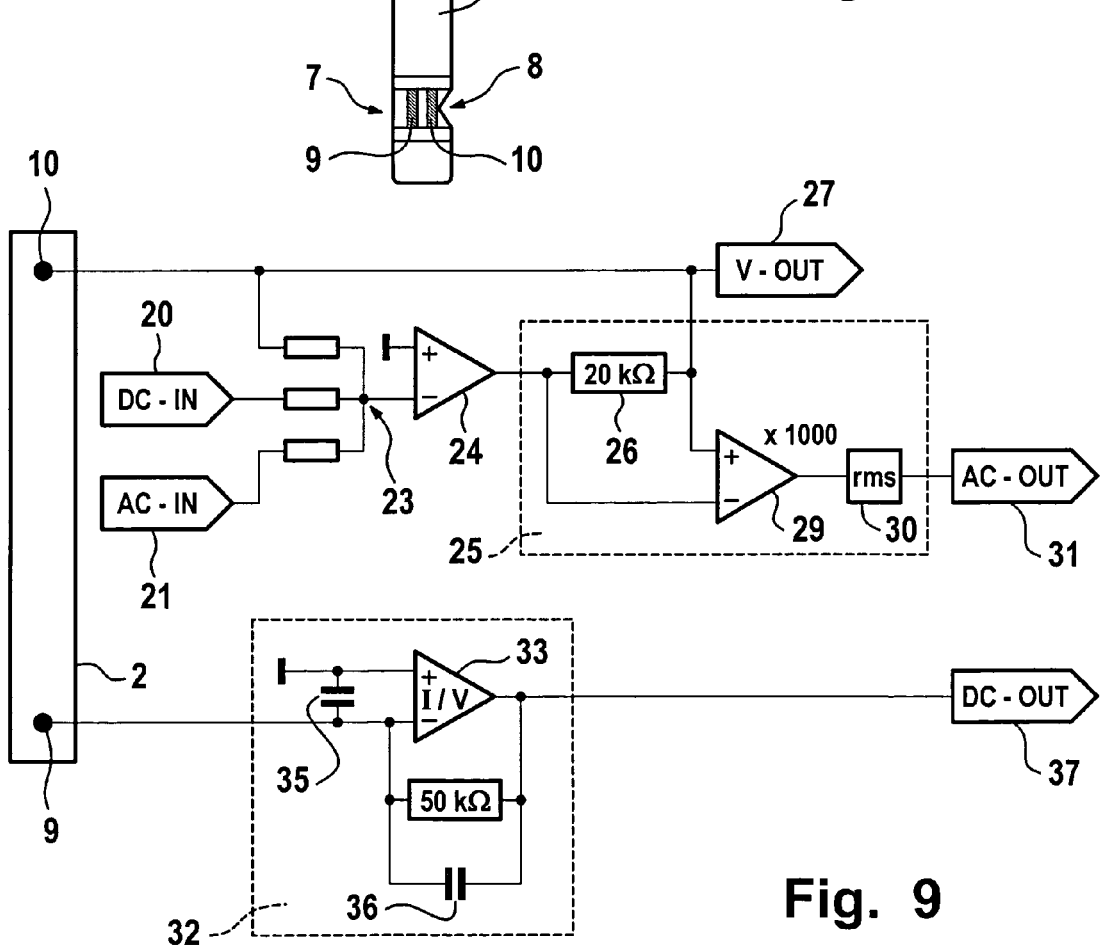
Fig. 8
Fig. 9

BIOSENSOR SYSTEM

REFERENCE TO RELATED APPLICATIONS

The present application is a Continuation of PCT Patent Application No. PCT/EP2004/002646, filed Mar. 13, 2004 which claims priority to European Patent Application No. 03008143.4, filed Apr. 8, 2003, which are hereby incorporated by reference in their entirety.

TECHNICAL FIELD

The invention relates to a system and method for the electrochemical determination of an analyte in a biological fluid sample. Such systems are often referred to as biosensor systems.

BACKGROUND

The concentration of a medically interesting analyte in a biological fluid is often determined by means of an electrochemical test. For example, a highly specific reaction between the analyte and a test reagent, generally an enzyme, may be carried out which causes a change of the oxidation stage of the enzyme. The degree to which this change takes place depends on the concentration of the analyte. The degree of the change is detected by means of a charge transfer to a solid electrode. The rate of charge transfer at the electrode is detected by applying a DC-voltage thereto and measuring the resulting DC-current. The concentration of the analyte is derived from this current measurement.

A typical reaction sequence of such an electrochemical test is shown in FIG. 1. An enzyme catalyzes an oxidation of an analyte A thereby forming an analyte product P. Simultaneously the enzyme is reduced from its oxidized form $E_{ox}$ to its reduced form $E_{red}$. By this highly specific enzymatic reaction an electron is transferred from the analyte to the enzyme. The enzyme cycles back to the oxidized form thereby transferring an electron to a mediator which is transferred from its oxidized form $M_{ox}$ to its reduced form $M_{red}$. The mediator is reoxidized by application of a DC-voltage, thereby transferring an electron to a solid state electrode EL.

Examples of the use of this test principle include glucose tests which can be used to monitor the blood sugar status of diabetics. This monitoring is of utmost importance both medically and commercially, because the health status of diabetics highly depends on reliable, easily generated data on their blood glucose level. The enzymes used in glucose testing are generally glucose oxidase or glucose dehydrogenase. Prominent mediators are ferrocen, ferrocyanide and phenylendiamine. Other enzymes and mediators are also available in the art.

As described herein, the present invention is useful with enzymatic amperometric tests, such as for glucose. It can, however, be useful with any amperometric test which includes an overall reaction sequence comprising the following redox reactions:

an analyte-specific redox reaction in a homogeneous (hydrated) phase by which a product is formed which can, with application of a suitable voltage, be oxidized or reduced at a solid electrode (also referred to as a "forward reaction");

a heterogeneous electrode reaction by which an electron is transferred from the product of the analyte-specific reaction to the electrode or from the electrode to the product (also referred to as a "reverse reaction" or "electrode reaction").

Clearly, each of these reactions may comprise a plurality of reaction stages. For example, the electrochemical test sequence that includes the formation of $M_{red}$ via the enzyme, as shown in FIG. 1, is a two-stage analyte-specific reaction. The mediator is, however, only needed if the direct charge transfer of the enzyme to the solid state electrode is too slow. Therefore, depending on the type of enzyme and electrode used, tests are also possible in which the mediator is omitted. On the other hand, the present invention may be used in electrochemical tests comprising several reaction stages.

Electrochemical tests are produced in numerous different formats including electrodes suitable for immersion into the sample liquid. The present invention is applicable to different formats. In one embodiment, use of the invention is directed to biosensor systems comprising disposable analysis elements and an evaluation instrument which is specifically adapted for evaluation thereof. Normally, the components of the system are developed and supplied by the same manufacturer. The analysis elements contain the reagent system required for a particular test (designated here as "analyte reactant") and at least two electrodes. The evaluation instrument of the system generally has a holder for receiving a disposable analysis element (also referred to herein as a "biosensor"). When the biosensor is plugged into the holder, an electrical contact is established between the electrodes of the biosensor and the instrument electronics.

In various embodiments of a biosensor, the analyte reactant may be contained in a porous matrix such as a paper or porous plastic element which is in contact with the electrodes and to which the sample is applied. In recent years, an alternative design of analysis elements has become increasingly important in which the analyte reactant and the electrodes are contained in a capillary space. The sample liquid is applied to an opening of the capillary space and drawn into the space by capillary action. The analyte reactant is at least partially hydrated by the sample liquid drawn into the space, thereby forming a reaction layer which is in contact with the electrodes provided with the biosensor for measuring the analyte detection current which corresponds to the analyte concentration in the sample liquid. Various embodiments of the present invention described herein relate generally to biosensor systems comprising such a "capillary biosensor". Nevertheless, a person of ordinary skill in the art of biosensor systems will understand and appreciate alternative embodiments of the invention including use of biosensors other than capillary biosensors, and such alternatives are intended to be within the scope of the claims appended hereto, except as may be otherwise recited therein.

More details about such biosensor systems can be taken from the appropriate literature. In particular, a capillary biosensor system is described in WO 99/32881 and this document contains an extensive list of earlier publications from which a substantial amount of additional technical information can be taken. The disclosure of this document and of the documents listed therein are incorporated herein by reference.

FIG. 2 is taken from U.S. Pat. No. 5,243,516 and shows a typical example of the timing sequence in prior art electrochemical tests. After an analysis element has been plugged into the evaluation instrument, a sample detection voltage is applied to the electrodes. Substantially no current flows as long as there is no sample in a sample well of the analysis element bridging the electrodes. However, as soon as the sample well is sufficiently filled, a current spike CS that exceeds a given threshold is sensed, indicating that a drop of sample has been dosed into the sample well of the analysis element and the resulting reaction layer formed by the sample and the analyte reactant bridges the electrodes. This point of time is designated "dose detect" (DD). After current spike CS has been sensed, the sample detect voltage is removed from the electrodes and the analyte-specific forward reaction takes place during an incubation period IP. After the incubation period IP, an analysis voltage suitable for the electrode reaction (reverse reaction) is applied to the electrodes. In one embodiment, the analysis voltage is larger than the sample detection voltage. In other embodiments, the analysis voltage is substantially the same as the sample detection voltage. The differences in selecting the value of the analysis voltage as compared to the sample detection voltage is generally understood and appreciated in the art to those of ordinary skill, for example as described in U.S. Pat. No. 5,243,516. FIG. 2 shows typical shapes of the resulting functional relationship I(t) of the current I versus time for four different values of the glucose concentration as indicated in the Figure. These curves of the DC-current versus time are hereafter designated "I(t)-traces".

If all required test conditions are met, the shape of the I(t)-traces corresponds (after a surge time ST in which the I(t)-trace is substantially influenced by the particulars of the measurement electronics) to a characteristic function proportional to $1/\sqrt{t}$. A deviation from this "Cottrell current curve" indicates deviations from the required test conditions. U.S. Pat. No. 5,243,516 proposes to make a plurality of current measurements at a plurality of measurement times during the period in which the reverse reaction takes place and to use a simple mathematical method to control whether the I(t)-traces as shown in FIG. 2 are in agreement with the Cottrell current. If this is not the case a malfunction of the system can be assumed and indicated.

Problems with accuracy of biosensor system measurement results are caused by sources of error which have effects on the biosensor output, such as temperature and other interferents. An example of an interferent factor is the concentration of red blood cells, i.e. hematocrit, in whole blood. This problem is discussed in the publication:

Tang et al.: "Effects of Different Hematocrit Levels on Glucose Measurement with Handheld Meters for Point-of-Care Testing", Arch Pathol Lab Med, 2000, pp. 1135 to 1140.

The authors point out that, even with the latest technology of biosensors, large errors of the glucose value on the order of 20 to 30% are caused by variations of the hematocrit which may occur in practice. A number of possible mechanisms by which these errors may be caused are mentioned. It is noted that solutions to this problem are badly needed but no means for compensation of the hematocrit error are described by those authors.

Another important source of error are temperature variations. Amperometric test results generally show a strong dependence on the temperature of the reaction layer. Therefore, in some biosensor systems, the temperature of the reaction layer is carefully controlled to a fixed value. In other systems the temperature is measured and a correction calculation is performed to compensate for temperature variations.

According to the above-mentioned WO 99/32881, an AC-measurement can be made to achieve a correction for the combined effect of sample temperature and hematocrit. To this end, an AC-voltage in the frequency range between about 2 kHz and about 10 kHz is applied to the electrodes, and the real and imaginary components of the impedance of the biosensor-sample system are determined. The magnitude and the phase angle of the impedance are calculated therefrom and a look-up table stored in the instrument is consulted for a correction factor. This correction factor is applied to conventionally determined glucose values, thereby deriving a corrected glucose concentration.

SUMMARY

In order to simplify the following description, we refer hereafter only to the example of enzymatic tests in which reaction A ("forward reaction") is an enzymatic reaction which leads to the formation of a reduced mediator and reaction B ("reverse reaction") is a reoxidation of the mediator by transfer of electrons to the electrode. This should, however, not be understood as a limitation of the general applicability of the invention to only 2-stage reaction sequences.

In order to achieve a very good accuracy of the detected concentration while simultaneously getting very fast results, one embodiment of the invention comprises a biosensor system for the electrochemical determination of an analyte concentration in a sample, the system comprising an analyte reactant and at least two electrodes, wherein the analyte reactant is at least partially hydrated by the sample liquid to form a reaction layer and the reaction layer is located to be in contact with the electrodes, in order to measure, upon application of an analysis voltage to the electrodes, an analyte detection current which corresponds to the analyte concentration in the sample liquid. The analyte detection current corresponds to the analyte concentration in the sample by virtue of a reaction sequence comprising an analyte-specific reaction taking place in the reaction layer and an electrode reaction including transfer of electrons through an electrode surface. Electronic circuitry is provided in the system and in electrical contact with the electrodes, the circuitry in one embodiment comprising a DC-voltage source for applying the analysis voltage to the electrodes, and measurement and evaluation electronics for measuring a plurality of values along a curve of the analyte detection current versus time over a plurality of measurement times and for deriving the analyte concentration therefrom. The analysis voltage is applied to the electrodes during the analyte-specific reaction whereby the analyte-specific reaction and the electrode reaction take place generally simultaneously resulting in an analyte detection current versus time curve which comprises a rising section in which the current increases over time to a maximum current (as a result of the kinetics of any effect that influences the rate of reaction, such as temperature, activity of the enzyme, etc., of the analyte-specific reaction and the kinetics of the electrode reaction). The analyte detection current is measured at at least two points of time in the rising section and the at least two measurements are used in an algorithm for interferent error compensation. A corresponding method is also proposed.

In other embodiments, a biosensor system for the electrochemical determination of an analyte concentration in a sample comprises an analysis element that is pluggable into an evaluation instrument, the analysis element having at least two electrodes and an analyte reactant, the evaluation instrument having electronic circuitry configured to apply an analysis voltage to the electrodes of the analysis element relatively immediately after a sample is detected on the analysis element and to measure a plurality of current values over time up to at least the time at which a maximum current value is measured, and to use the plurality of values in an algorithm for interferent error compensation.

In yet other embodiments, a biosensor system for the electrochemical determination of an analyte concentration in a sample comprises an analysis element that is pluggable into an evaluation instrument, the analysis element having at least two electrodes and an analyte reactant, the evaluation instrument having electronic circuitry configured to apply an analysis voltage to the electrodes of the analysis element relatively immediately after a sample is detected on the analysis element and to measure a plurality of current values over time up to at least the time at which a maximum current value is measured, and to use the plurality of values in an algorithm for interferent error compensation. The electronic circuitry is further configured to apply an AC-voltage to the electrodes and to measure resulting AC current, the measured AC current being used in the evaluation algorithm.

In yet other embodiments, a biosensor system for the electrochemical determination of an analyte concentration in a sample comprises an analysis element that is pluggable into an evaluation instrument, the analysis element having at least two electrodes and an analyte reactant, the evaluation instrument having electronic circuitry configured to apply an analysis voltage to the electrodes of the analysis element relatively immediately after a sample is detected on the analysis element and to measure a plurality of current values over time up to at least the time at which a maximum current value is measured, and to use the plurality of values in an algorithm for interferent error compensation. The electronic circuitry is further configured to apply an AC-voltage to the electrodes and to measure resulting AC current, the measured AC current being used in the evaluation algorithm, the evaluation algorithm including determining a baseline-corrected current measurement value for the plurality of values, normalizing the time scale of the I(t)-trace according to a ratio of measurement time to the time of the maximum current value, and transforming the plurality of values based on the time normalized current measurement values and impedance values calculated from the AC current values.

In yet other embodiments, an evaluation instrument for use with an analysis element having at least two electrodes and an analyte reagent comprises electronic circuitry configured to apply an analysis voltage to the electrodes relatively immediately after a sample is detected at the electrodes, and to measure a plurality of current values over time resulting from the application of the analysis voltage, up to at least the time at which a maximum current value is measured, and to use the plurality of values in an algorithm for interferent error compensation. The electronic circuitry is further configured to apply an AC-voltage to the electrodes and to measure resulting AC current, the measured AC current being used in the evaluation algorithm.

These and other features and advantages of the present invention will be more fully understood from the following detailed description of the embodiments of the invention taken together with the accompanying claims. It is noted that the scope of the claims is defined by the recitations therein and not by the specific discussion of the features and advantages set forth in the present description.

BRIEF DESCRIPTION OF THE DRAWINGS

The inventors have found that an error compensation which is both fast and accurate can be achieved by using current measurement values from a very early stage of the analysis reaction. This becomes better understandable from the following description in combination with the Figures, wherein:

FIG. 8 shows a top view of the components of a typical biosensor system to which an embodiment of the present invention may apply;

FIG. 9 shows a schematic diagram of parts of suitable electronic circuitry for an evaluation instrument for the system of the present invention.

Skilled artisans appreciate that elements in the Figures are illustrated for simplicity and clarity and have not necessarily been drawn to scale. For example, the dimensions of some of the elements in the Figure may be exaggerated relative to other elements to help improve understanding of the embodiment(s) of the present invention.

In order that the invention may be more readily understood, reference is made to the following examples, which are intended to illustrate the invention, but not limit the scope therof.

DETAILED DESCRIPTION

The following description of the preferred embodiment is merely exemplary in nature and is in no way intended to limit the invention or its application or uses.

Although the disclosure hereof is detailed and exact in order to enable those skilled in the art to practice the invention, the physical embodiments herein disclosed merely exemplify the invention which may be embodied in other specific structure. The scope of the invention is defined in the claims appended hereto.

Figure 1:
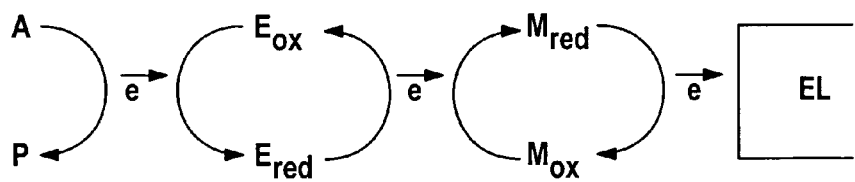
FIG. 1 shows a graphical representation of a typical analysis reaction sequence.
Figure 2:
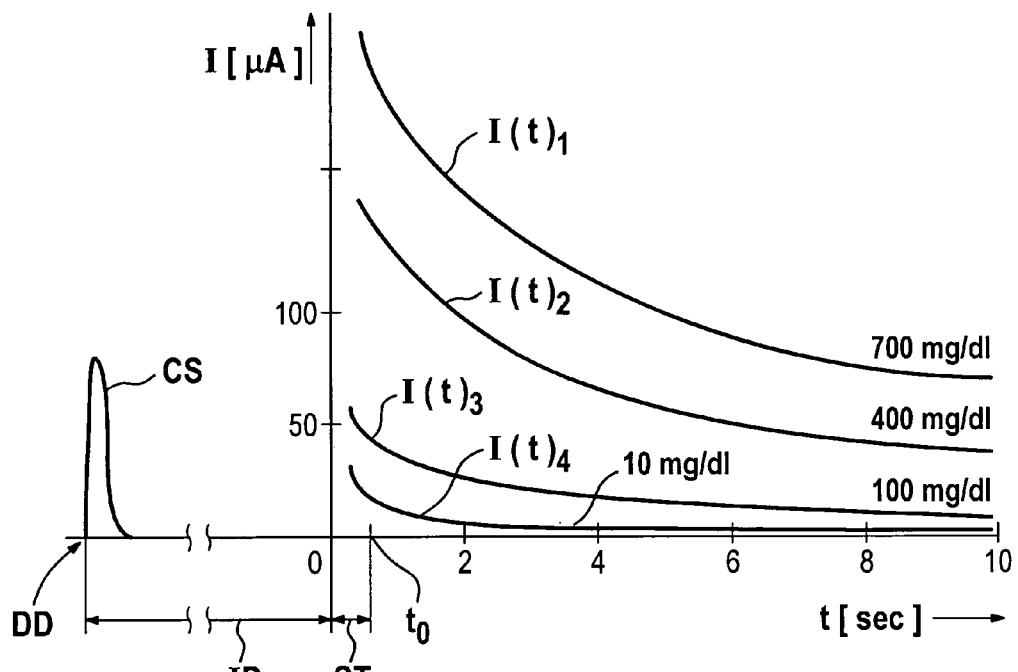
FIG. 2 shows a graphical representation of DC-current versus time measured in a test according to the prior art.

As discussed above, FIG. 2 shows an I(t)-trace resulting from a prior art test sequence in which an analysis voltage is applied across the electrodes of a biosensor after an incubation period in which the analyte-specific forward reaction can take place. If, however, the analysis voltage is applied relatively immediately after dose detect DD, a different I(t)-trace results from which information can be utilized for correction of errors caused by interferents such as temperature and hematocrit.

Figure 3:
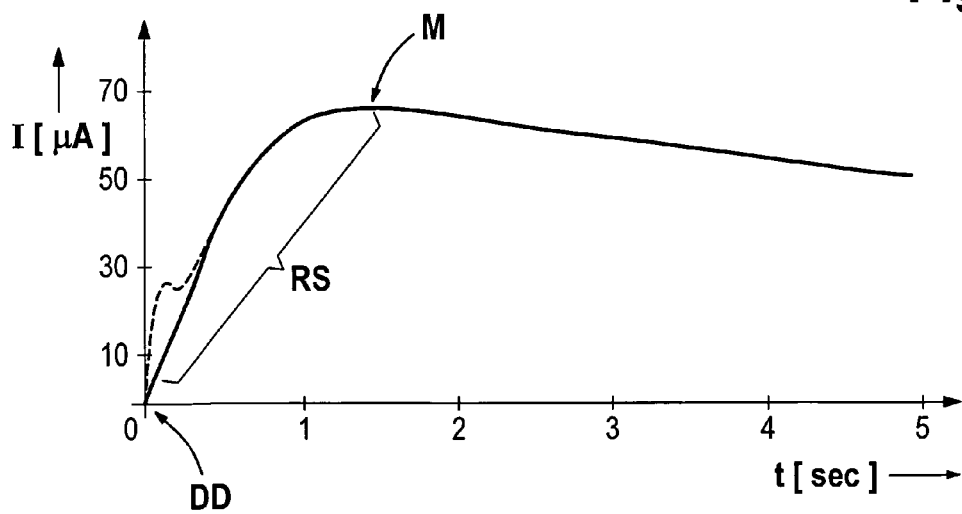
FIG. 3 shows a graphical representation of DC-current versus time measured in a test according to an embodiment of the present invention.

FIG. 3 shows a typical shape of an I(t)-trace which results when the analysis voltage (DC-voltage required for driving the reverse reaction) is applied not at the end of an incubation period for the analyte-specific forward reaction but rather at a much earlier point of time. In one embodiment, the analysis voltage is applied substantially at dose detect DD. In other embodiments, the analysis voltage is applied within no more than about 500 milliseconds after dose detect DD. In yet other embodiments, the analysis voltage is applied within no more than about 300 milliseconds after dose detect DD. In yet other embodiments, the analysis voltage is applied within no more than about 100 milliseconds after dose detect DD. For convenience, in one embodiment, no special sample detect voltage is used but rather the analysis voltage is applied after the biosensor is plugged into the instrument and before the sample is contacted to the electrodes. Dose detection typically occurs when a sufficient volume of sample has been supplied to the analysis element to wet or hydrate (either partially or wholly) the analyte reagent and bridge the gap separating the at least two electrodes with the resulting hydrated reaction layer, such as a hydrogel or other hydrated phase.

The shape of the I(t)-trace shown in FIG. 3 is the result of a rather complicated combination of a plurality of influencing factors. In particular, the shape depends on the speed of the enzymatic reaction of the forward reaction. The enzymatic reaction depends not only on the concentration of the analyte but also on a plurality of potentially interfering factors, such as the type of enzyme, temperature, and the diffusion of the reactants (which itself is influenced by the temperature as well as the presence of components, blood cells for example, in the sample). The product generated by the enzymatic reaction is simultaneously consumed in the reverse reaction occurring at an electrode, which is also influenced by a plurality of factors, mainly by the concentration of the product of the enzymatic reaction in the vicinity of the electrode surface which again depends on the diffusion conditions in the sample liquid. In any case, it is characteristic for the invention that the I(t)-traces include an initial section in which the DC-current resulting from application of the analysis voltage increases versus time. This section is designated rising section RS.

It has to be noted that an I(t)-trace measured in practice may have a more complicated shape, depending on the experimental setup. In particular, it may not be monotonically rising in the rising section after application of the analysis voltage. Rather there may be an intermediate maximum as shown in dashed line in FIG. 3. Such a shape is, however, not typically due to the reaction sequence explained but rather due to transient behavior of the experimental setup, such as the measurement electronics. The rising section of the I(t)-trace as defined herein is the section preceding the maximum current M which is due to the reverse reaction in the redox reaction sequence.

In the context of the present invention it has been found that, in spite of this complicated situation, measured values of the analyte detection current which are taken at points of time within the rising section RS of the I(t)-trace (before it reaches its maximum current M) can be used to improve the quality of the analytical result derived from the measurement. In one embodiment, by measuring the DC-current value at at least two points of time in the rising section RS it is possible to compensate for errors caused by variations of the temperature of the reaction layer. It is also possible to derive the analyte concentration itself from current measurement values in the rising section RS.

Additional error corrections, such as to compensate for errors caused by variations of the hematocrit values of the sample, are possible if AC-current measurements are also performed during the rising section of the I(t)-trace. That is, an AC-voltage is applied generally simultaneously with the DC-voltage and the resulting AC-current is measured. In one embodiment, measurements of the DC-current and of the AC-current are performed generally simultaneously, i.e. there is an at least partial overlap of the measurement periods during which the DC- and AC-current measurements are performed.

The present invention achieves superior results regarding analytical tests at high speed and with very good analytical quality. In this context it has to be noted that enzymes providing a high specificity for a particular analyte generally react relatively slowly. With the classical method, this increases the time required for the incubation period and therefore the time required for generating the analytical result. If enzymes are used which are optimized for short reaction times, this generally requires a reduction of the specificity and thus of the quality of the test. As described herein, the present invention, on the other hand, fulfills both requirements (high specificity and fast response) at the same time.

FIGS. 4 to 7 show results from experimental work performed in the context of the present invention in connection with a biosensor system configured to determine the concentration of glucose in whole blood.

Figure 4:
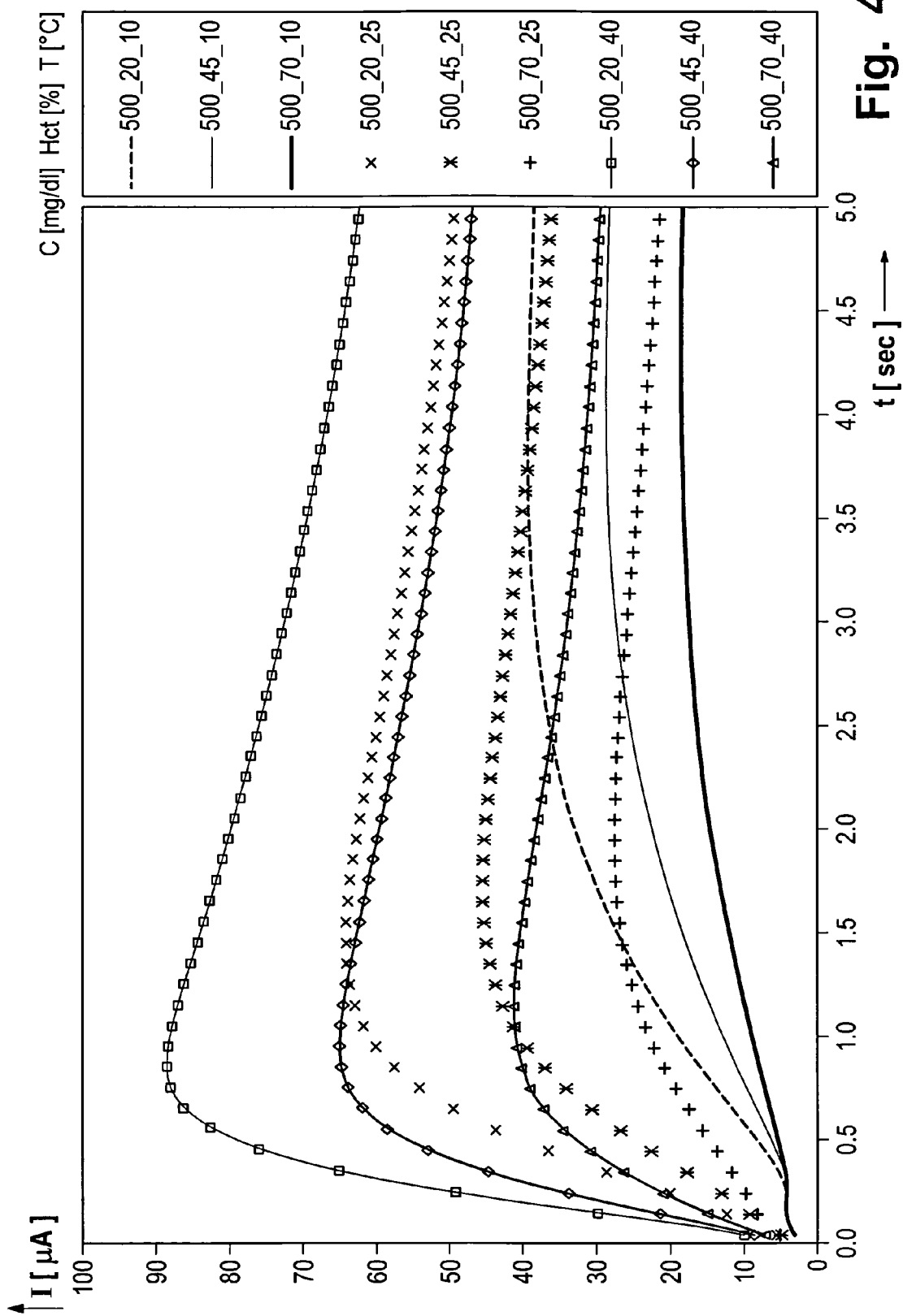
FIG. 4 shows a graphical representation corresponding to FIG. 3 for the same analyte concentration but a plurality of different temperatures and hematocrit values of the reaction liquid.

FIG. 4 shows I(t)-traces as in FIG. 3, i.e. with the analysis voltage applied substantially at dose detect, for a single glucose concentration (500 mg/dl) but for varying values of the hematocrit and of the reaction liquid temperature. The graph shows curves for three hematocrit values (20%, 45% and 70%) and three temperatures (10°, 25° and 40° C.) each. The individual I(t)-traces are distinguished by using different symbols as shown in the column on the right side of the graphs. The same symbols are also used in FIGS. 5 and 6.

The data were derived from the original current measurements applying a baseline correction:

$$I_{BC}(t) = I_{org}(t) - C \times (t^{-1/2} \times e^{0.1/t})$$

wherein
$I_{BC}$: baseline corrected current
$I_{org}$: original Current
C: empirical constant This baseline correction subtracts contributions caused by electrical charge carriers contained in the sample but not relating to the glucose concentration ($t^{-1/2}$-term) and by the damping effect of the measurement electronics ($e^{0.1/t}$-term).

A further correction to the data was necessary in view of the fact that it is not possible to prepare samples having exactly the desired values of the glucose concentration and of the hematocrit. Rather, the samples had to be prepared by diluting available whole blood samples and adding glucose as required. Resulting minor deviations from the exact values shown in FIG. 4 were corrected by linear regression.

FIG. 4 shows the following characteristics:
Each of the curves includes a rising section essentially starting at dose detect (time≈0) up to a maximum current M.
The position of the maximum current M on the time scale depends on the temperature. The higher the temperature, the earlier the maximum current M occurs. The drop of the I(t)-trace after the maximum is not visible for the 10° C.-traces because it occurs after the maximum measurement time (5 sec) shown. It is, however, possible to electronically detect a maximum current M with each of the traces.
For each temperature, the hematocrit causes a shift of the I(t)-trace: An increase of the hematocrit causes a decrease of the measured current values.

Figure 5:
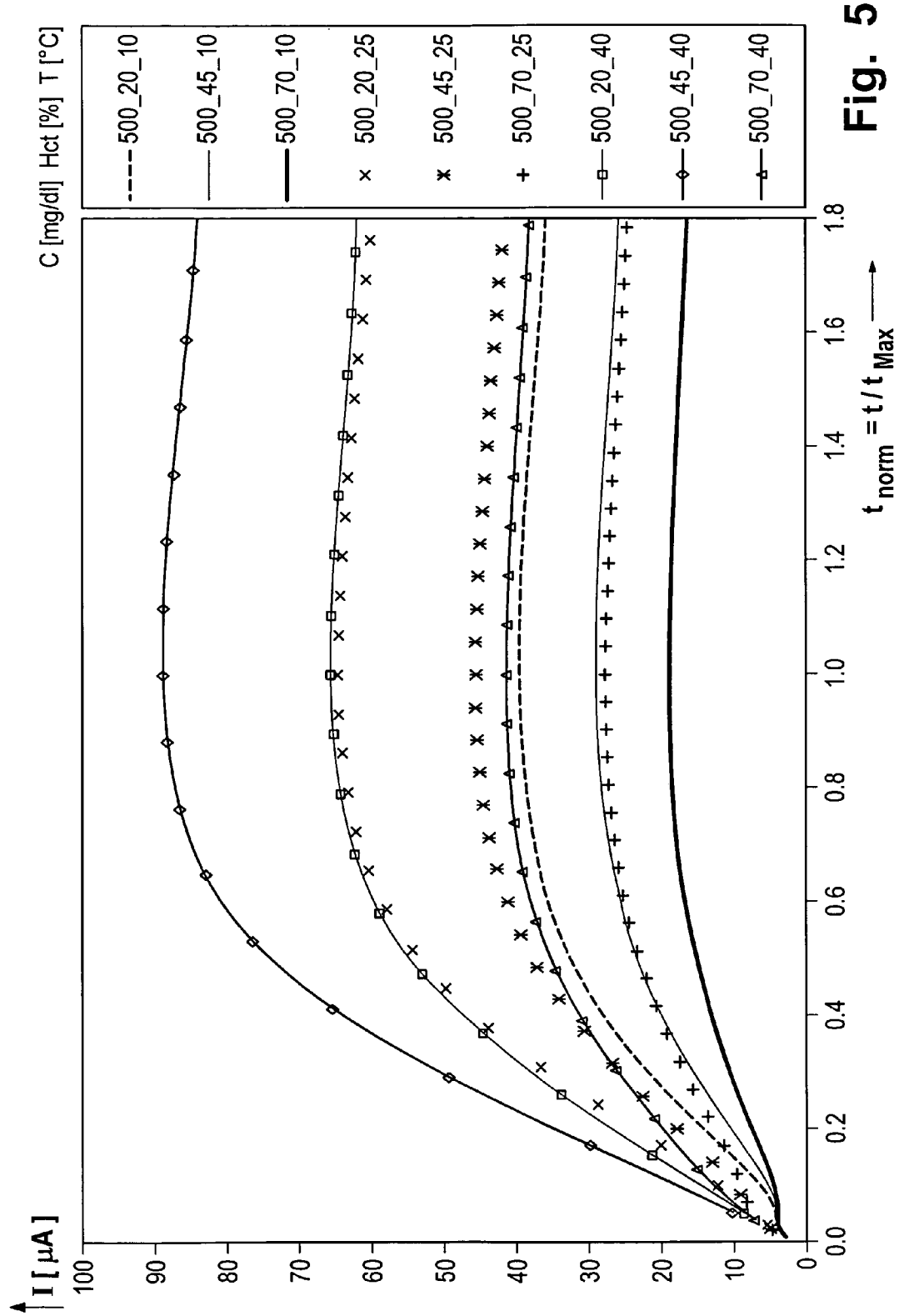
FIG. 5 shows a graphical representation corresponding to FIG. 4 but with a normalized time axis.
Figure 6:
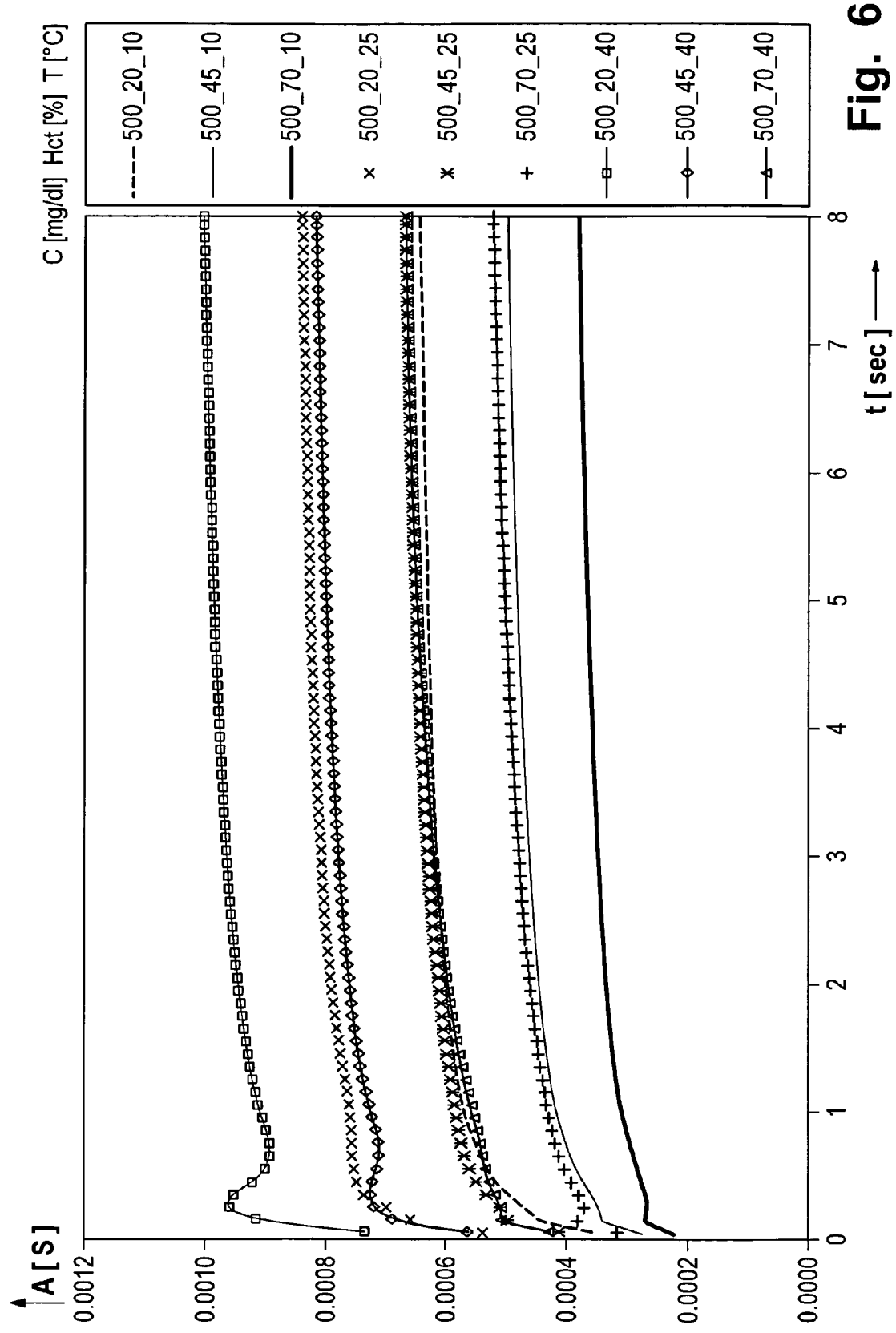
FIG. 6 shows a graphical representation of AC-current versus time for the same analyte concentration but a plurality of different temperatures and hematocrit values of the reaction liquid.

FIG. 5 shows the same data as FIG. 4 but with a normalized time scale according to:

$$t_{norm} = t/t_{max}$$

wherein
$t_{max}$: time after dose detect at which the maximum of the respective I(t)-trace occurs FIG. 6 shows the results derived from AC-current measurements, with an applied AC-voltage having a frequency of 2 kHz versus time for the same samples as FIG. 4. The derived quantity shown is the admittance A (reciprocal of impedance Z) measured in S ($Ohm^{-1}$). The curves show relatively strong initial variations which relate to the transient behavior of the measurement electronics. After at most two seconds, however, a stable value is achieved which shows only a very slow increase in admittance versus time which is due to a strong damping of the electronics used for the experiments.

Figure 7:
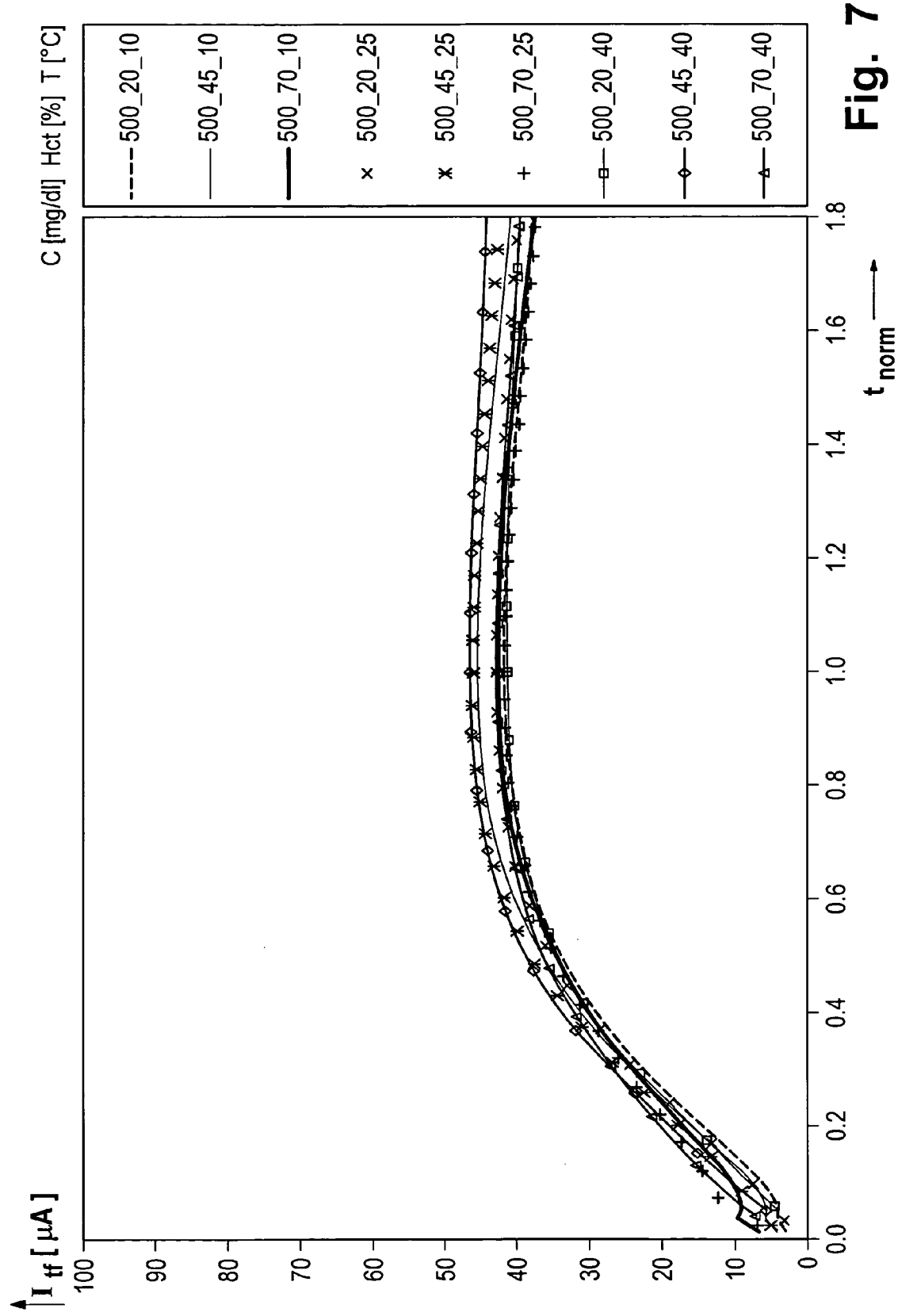
FIG. 7 shows a graphical representation corresponding to FIG. 5 but with a linear transformation of the current values.

FIG. 7 shows the same data as FIG. 5 but after a transformation of the current values according to:

$$I_{tf} = I_{norm} \times (1 + \text{deltaZ} \times A)$$

wherein $I_{norm}$ is the current value versus $t_{norm}$ such as in FIG. 5, and deltaZ is calculated according to:

$$\text{deltaZ} = (Z - Z_{med})$$

wherein

Z is impedance measured between the electrodes with an AC-voltage of 2 kHz at a point of time after the initial Z variations (e.g. at 3 sec in FIG. 6).

$Z_{med}$: Median of the Z values at this point of time

A is an empirically determined weighing factor for optimum coincidence of the curves shown in FIG. 7.

The series of FIGS. 4 to 7 shows that, by relatively simple mathematical steps, the complicated shape of the I(t)-traces shown in FIG. 4 can be reduced to essentially a single coinciding curve as shown in FIG. 7. In other words the I(t)-traces shown in FIG. 4 having a non-linear dependence on temperature and hematocrit can be transformed to I(t)-traces having a linear dependence on these interfering factors by using a suitable transformation of the time axis.

These results show that—in contrast to the prior art—reliable results, including correction for such interfering factors as temperature and hematocrit, can be derived from amperometric measurements in which the enzymatic forward reaction takes place simultaneously with the reverse reaction. Furthermore, it is possible to use current measurement values from the rising section of the I(t)-traces to do this. This again enables substantial reduction in the required time for performing a measurement because it is not necessary to introduce an incubation period for first performing the forward reaction. It is also not necessary to wait until the forward reaction and the reverse reaction lead to a steady state in which the mediator is generated with the same speed in which it is consumed, i.e. its concentration is constant.

One embodiment of a method of performing an analysis of a sample having an unknown glucose concentration comprises the following steps:

measuring an I(t)-trace as shown in FIG. 3;
performing a baseline correction;
determining $t_{max}$;
identifying a current value measured at a time which corresponds to a predetermined point of time on the normalized time axis (e.g. $0.7 \times t_{max}$) for further evaluation;
correcting this current value on the basis of an AC measurement; and
transforming the resulting corrected current to a glucose concentration based on a calibration performed for the same point of time on the normalized time axis (e.g. $0.7 \times t_{max}$).

This, however, is only one of several possibilities to evaluate current versus time measurements made in accordance with the present invention. FIGS. 4 to 7 show that the shape of the rising section of the I(t)-traces is characteristic for the combination of the influencing factors including a "variance" (the concentration of the analyte, e.g. glucose) and a plurality of "covariances" (interfering factors such as temperature and hematocrit). Therefore the effects of the covariances can be separated and consequently eliminated by measuring a plurality of values of the DC-current in the rising section of the I(t)-trace and by feeding these values into a suitable algorithm.

In an exemplary alternative embodiment to the described mathematical-analytical method, numerical methods may be used for this purpose. Such numerical methods include different types of multivariate analysis. Computer programs for performing such methods are commercially available. They generally include a calibration which has to be performed by the manufacturer of the biosensor system using a plurality of samples with different hematocrit and measurements at different temperatures. The results of such calibration can then be programmed into the instrument for use during analysis of samples with unknown values of glucose and hematocrit concentrations on the basis of measurements at arbitrary temperatures within the temperature range for which the instrument was trained.

The interferent correction may in principle be based on only two values of the analyte detection current measured within the rising section of the I(t)-trace. In one embodiment, information regarding the curvature of the I(t)-trace is also included into the correction algorithm. This requires measurement of at least three values of the analyte detection current at different points of time during the rising section of the I(t)-trace.

The rising section of the I(t)-trace generally shows a strong dependence on any factor having an effect on the kinetics of the forward reaction, e.g. the measurement temperature of the sample, and therefore values from the I(t)-trace in this section are valuable in compensating for errors caused by such factors. As has been stated, temperature and hematocrit are prime examples of such kinetics-effecting factors, also referred to generally herein as "interferents". In one embodiment, the evaluation algorithm may additionally include measurement data generated at a point of time after the maximum current M of the I(t)-trace. Such data can be of interest with respect to the sensitivity to changes of the analyte concentration and/or with respect to the quality of the hematocrit correction. In other embodiments, the measurement of the I(t)-trace is terminated after the maximum current M of the I(t)-trace has been detected. This allows especially short measurement times if the temperature is relatively high (such as room temperature) and therefore the maximum current M is reached shortly after dose detect. On the other hand, if a measurement has to be performed at a low temperature (e.g. during an out of house activity of the user) the instrument waits to terminate measurement of the I(t)-trace until the maximum current M has been detected, thereby allowing a high-accuracy measurement with a measurement time which is slightly larger but still as short as possible. As a result, embodiments of the present invention include measurement systems and sequences adaptive to the velocity of the forward reaction in order to minimize the total time required to achieve accurate test results.

An embodiment of a biosensor system 1 according to the present invention is shown in FIG. 8 and comprises a disposable analysis element 2 and an evaluation instrument 3. Evaluation instrument 3 has a holder 4 for receiving and holding an analysis element 2. When analysis element 2 is inserted into evaluation instrument 3, electrical connection is established by cooperation of electrical contacts 6, provided at analysis element 2, cooperating with mating contacts (not shown) of the instrument 3.

In one embodiment, analysis element 2 has a reaction zone 7 comprising a sample application opening 8 for applying a drop of sample. From opening 8, a narrow capillary space (not shown) extends to two electrodes 9, 10 where the capillary space contains an analyte reactant (not shown). The dimensions of the capillary space are such that the sample liquid applied to the sample application opening 8 easily penetrates thereinto, at least partially hydrates the analyte reactant and contacts both electrodes 9 and 10. Thereafter, the above described reaction and evaluation steps take place.

In order to make the required electrical measurements and to derive the analyte concentration in the sample from the measured current values, instrument 3 contains suitable electronic circuitry. In one embodiment, the electronic circuitry generally includes DC- and AC-voltage sources, DC- and AC-current measurement circuits and a microprocessor-controlled evaluation system which controls the instrument operation and causes the instrument 3 to perform the steps of the evaluation algorithm by which the desired analyte concentration is derived from the measured data.

Both with respect to the reagent chemistry and physical design of the analysis element 2 and with respect to the electronic circuitry of the instrument 3, system 1 is largely conventional (with the exception of particular features described herein). Therefore no more detailed description is required. Rather, any further information which may be of interest can be taken from the appropriate literature as cited herein.

FIG. 9 is a schematic representation of the basic design features of one embodiment of electronic circuitry that is suitable for simultaneously applying DC- and AC-voltages to the electrodes of a biosensor and measuring the resulting DC- and AC-current without mutual interference of the measurements.

As shown in the illustrated embodiment, the required DC and AC voltages are generated by respective voltage sources 20 and 21 and summed at a summing point 23 connected to the inverting input of an operational amplifier 24 which functions as a voltage follower. It provides at its output a low impedance source of the required DC and AC voltages which is connected via a shunt resistor 26 to one of the electrodes (namely electrode 10) of the analysis element 2. In order to allow monitoring of the voltage signal applied to electrode 10, a monitoring output 27 is provided.

Shunt resistor 26 belongs to an AC measurement circuit 25. The current flowing through shunt resistor 26 is measured by means of a differential amplifier 29 the output of which is proportional to the voltage drop at the shunt resistor 26 and thus of the current flowing therethrough. By means of an rms module 30 (rectifier-integrator), an output 31 corresponding to the rms-value of the AC-current flowing between the electrodes 9 and 10 is generated.

The DC-current flowing between electrodes 9 and 10 is measured by a separate current measurement circuit 32 which is independent of AC measurement circuit 25. It comprises a further operational amplifier 33 arranged and functioning as a current to voltage (I/V)-converter. Here, the AC-signal is filtered out by a suitable filtering arrangement including (in the embodiment shown) two capacities 35,36 parallel to the input and parallel to the feedback resistor of the I/V-converter. Thus the DC output 37 of the I/V-converter is proportional to the DC-current flowing between the electrodes 9 and 10. All outputs 27, 31 and 37 are digitized and transmitted to a microprocessor system of the instrument for further processing as described.

A person of ordinary skill in the art will understand and appreciate that other suitable arrangements of electronic circuitry are possible, and any such suitable arrangements that may be useful for carrying out the analysis described herein are intended to be within the scope of the claims appended hereto, except as may be otherwise recited therein.

Figure 10:
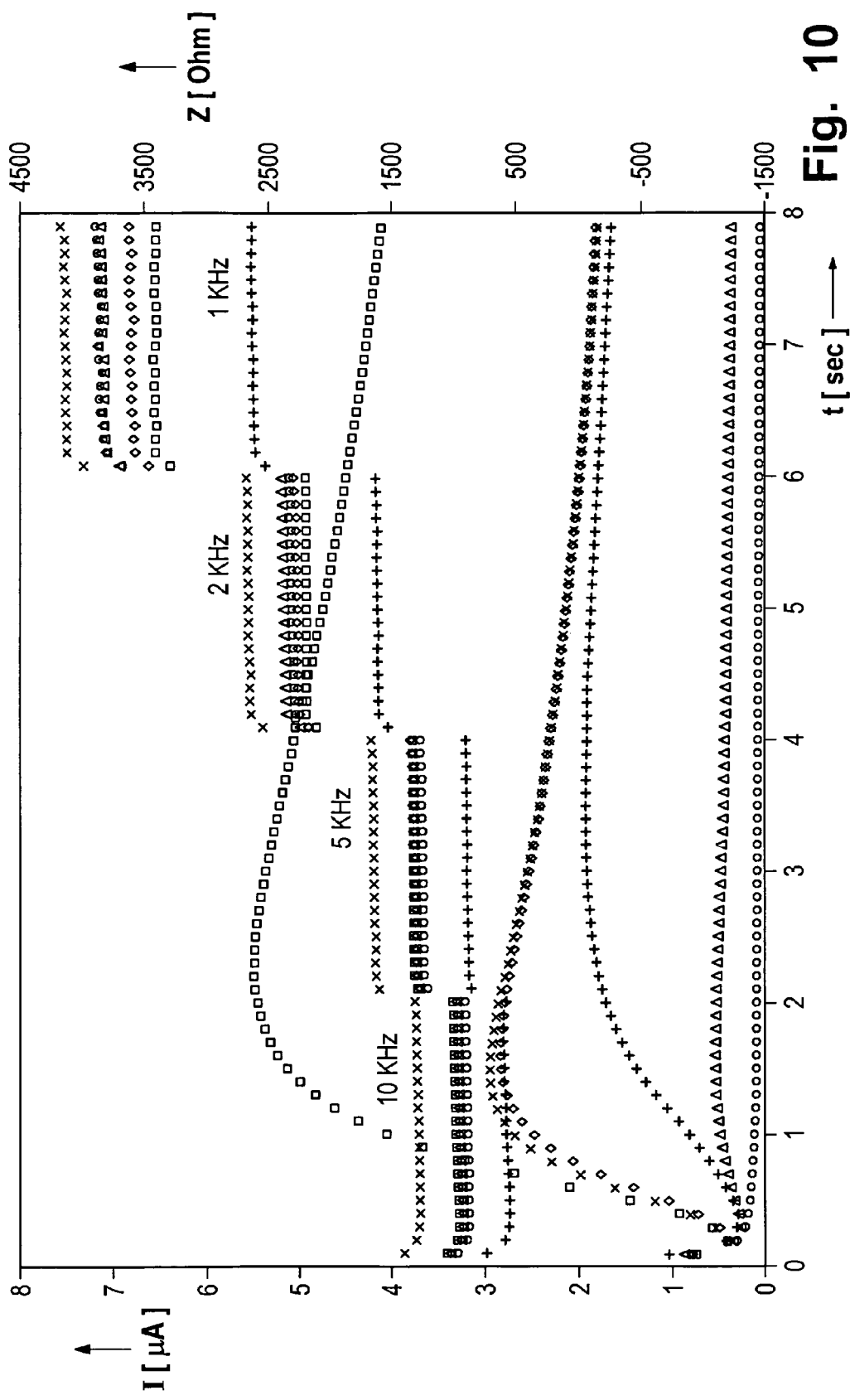
FIG. 10 shows a combined view of DC current and AC current measurements performed with the circuitry of FIG. 9.

FIG. 10 shows current and admittance measurements which were made with an embodiment of electronic circuitry according to FIG. 9. The I(t)-traces shown refer to a plurality of different sample solutions. The corresponding DC-current scale is shown on the left ordinate. Simultaneously FIG. 10 shows impedance values (right ordinate) measured by an AC-measurement with switching of a plurality of different frequencies as shown. Again the same sample solutions were used and corresponding traces are marked by the same symbols. FIG. 10 clearly shows that the AC- and DC-measurements are completely independent: There is no substantially evident variation of the DC-current signal at the points where the AC-voltage was applied and a corresponding sudden change of the AC-current was detected.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention may be identified herein as preferred or particularly advantageous, it is contemplated that the present invention is not necessarily limited to those aspects of the invention.

What is claimed is:

1. Biosensor system for the electrochemical determination of an analyte concentration in a sample, the system comprising an analyte reactant and at least two electrodes, wherein the analyte reactant is at least partially hydrated by the sample to form a reaction layer in contact with the electrodes for measurement of an analyte detection current flowing between the electrodes in response to an analysis voltage applied thereto, the analyte detection current corresponding to the analyte concentration in the sample by virtue of a reaction sequence comprising an analyte-specific reaction taking place in the reaction layer and an electrode reaction including transfer of electrons through a surface of one of the electrodes; and electronic circuitry comprising a DC-voltage source for applying the analysis voltage to the electrodes and measurement and evaluation electronics for measuring a plurality of values along a curve of the analyte detection current versus time over a plurality of measurement times and for deriving the analyte concentration therefrom by means of an evaluation algorithm;

wherein the analysis voltage is applied to the electrodes during the analyte-specific reaction, the analyte-specific reaction and the electrode reaction taking place generally simultaneously and resulting in an analyte detection current versus time curve which comprises a rising section in which the current increases versus time; and wherein the analyte detection current is measured at at least two points of time in the rising section and the values of the analyte detection current resulting from said at least two measurements are used in the evaluation algorithm for interferent error compensation.

2. System according to claim 1, further comprising a disposable analysis element including the analyte reactant and the at least two electrodes, and an evaluation instrument including the electronic circuitry and adapted for evaluation of the analysis element, the evaluation instrument further having a holder for receiving the analysis element and electrical contacts establishing an electrical connection to the analysis element when plugged into the holder thereby connecting the electrodes of the analysis element to the electronic circuitry.

3. Biosensor system according to claim 2, wherein the analysis element comprises a capillary-type biosensor including a capillary space, the electrodes and the analyte reactant being provided in the capillary space.

4. System according to claim 1, wherein the analyte detection current is measured at at least three points of time in the rising section to generate information about the shape of the rising section and the at least three values of the analyte detection current resulting from said at least three measurements are used in the evaluation algorithm for the interferent error compensation.

5. System according to claim 1, the electronic circuitry further comprising an AC-voltage source for applying an AC-voltage to the electrodes, and wherein the resulting AC-current is measured and used in the evaluation algorithm for the interferent error compensation.

6. System according to claim 5, wherein measurement of the AC-current is performed generally simultaneously with measurements of the analyte detection current in the rising section.

7. System according to claim 6, wherein the electronic circuitry further comprises DC- and AC-current measurement circuits for measuring the analyte detection current and the AC-current respectively.

8. System according to claim 7, wherein the DC-current measurement circuit is in electrical connection with one of said at least two electrodes and the AC-current measurement circuit is in electrical connection with the other of said at least two electrodes.

9. System according to claim 7, wherein the AC-current measurement circuit comprises a shunt resistor coupled to a differential amplifier.

10. System according to claim 7, wherein the DC-current measurement circuit comprises an operational amplifier-based voltage-to-current converter.

11. System according to claim 7, wherein the sample is whole blood and the error compensation based on the AC-current measurement comprises a compensation for variations of the hematocrit value of the whole blood sample.

12. System according to claim 1, wherein the use of the evaluation algorithm comprises a determination of a maximum current value of the analyte detection current versus time curve and use of a value of the analyte detection current versus time curve which has been measured at a point of time corresponding to a predetermined ratio to the point of time at which the maximum current value occurs.

13. System of claim 1, wherein the interferent for which the error compensation is made by the evaluation algorithm comprises any factor having an effect on the kinetics of the analyte-specific reaction.

14. System of claim 13, wherein the sample comprises whole blood, and the factor is at least one of the interferents selected from the group consisting of sample temperature and hematocrit.

15. Method for the electrochemical determination of an analyte concentration in a sample, comprising the steps of
at least partially hydrating an analyte reactant with the sample to form a reaction layer,
contacting the reaction layer to at least two electrodes,
applying an analysis voltage to the electrodes,
measuring a plurality of values of a curve of an analyte detection current versus time over a plurality of measurement times, the analyte detection current flowing between the electrodes in response to the analysis voltage and corresponding to the analyte concentration in the sample by virtue of a reaction sequence comprising an analyte-specific reaction taking place in the reaction liquid and an electrode reaction including transfer of electrons through a surface of one of the electrodes, and
deriving the analyte concentration by means of an evaluation algorithm comprising use of said plurality of values of the analyte detection current,
wherein the analysis voltage is applied to the electrodes during the analyte-specific reaction whereby the analyte-specific reaction and the electrode reaction take place generally simultaneously resulting in an analyte detection current versus time curve which comprises a rising section in which the current increases versus time; and
wherein the analyte detection current is measured at at least two points of time in the rising section and the values of the analyte detection current resulting from said at least two measurements are used in the evaluation algorithm for interferent error compensation.

16. Method according to claim 15, wherein the analyte detection current is measured at at least three points of time in the rising section to generate information about the shape of the rising section and the at least three values of the analyte detection current resulting from said at least three measurements are used in the evaluation algorithm for the interferent error compensation.

17. Method according to claim 15, further comprising the steps of applying an AC-voltage to the electrodes and measuring the resulting AC-current for use in the evaluation algorithm for interferent error compensation.

18. Method according to claim 17, wherein measuring the AC-current is performed generally simultaneously with measuring of the analyte detection current in the rising section.

19. Method according to claim 18, wherein the sample is whole blood and the error compensation based on the AC-current measurement comprises a compensation for variations of the hematocrit value of the whole blood sample.

20. Method according to claim 18, further comprising the step of providing electronic circuitry comprising DC- and AC-current measurement circuits for performing the steps of measuring the analyte detection current and the AC-current respectively.

21. Method according to claim 20, wherein the DC-current measurement circuit is provided in electrical connection with one of said at least two electrodes, and the AC-current measurement circuit is in electrical connection with the other of said at least two electrodes.

22. Method according to claim 20, wherein the AC-current measurement circuit comprises a shunt resistor coupled to a differential amplifier.

23. Method according to claim 20, wherein the DC-current measurement circuit comprises an operational amplifier based voltage to current converter.

24. Method according to claim 15, wherein use of the evaluation algorithm comprises a determination of a maximum current value on the analyte detection current versus time curve and use of a value of the analyte detection current versus time curve which has been measured at a point of time corresponding to a predetermined ratio to the point of time at which the maximum current value occurs.

25. Method of claim 13, wherein the interferent for which the error compensation is made by the evaluation algorithm comprises any factor having an effect on the kinetics of the analyte-specific reaction.

26. Method of claim 25, wherein the sample comprises whole blood and the factor is at least one of the interferents selected from the group consisting of sample temperature and hematocrit.

27. A biosensor system for the electrochemical determination of an analyte concentration in a sample comprising an analysis element that is pluggable into an evaluation instrument, the analysis element having at least two electrodes and an analyte reactant, the evaluation instrument having electronic circuitry configured to apply an analysis voltage to the electrodes of the analysis element relatively immediately after the sample is detected on the analysis element and to measure a plurality of current values over time up to at least the time at which a maximum current value is measured, and to use the plurality of values in an algorithm for interferent error compensation.

28. The system of claim 27, the electronic circuitry further being configured to apply an AC-voltage to the electrodes generally simultaneously with application of the analysis voltage and to measure resulting AC-current over substantially the same time, the measured AC-current being used in the evaluation algorithm.

29. The system of claim 28, the use of the evaluation algorithm comprising determining a baseline-corrected current measurement value for the plurality of values, normalizing the times at which the plurality of values are each measured according to a ratio of measurement time to the time of the maximum current value, and transforming the plurality of values based on the time-normalized current measurement values and impedance values calculated from the measured AC-current.

30. The system of claim 27, wherein the interferent for which the error compensation is made by the evaluation algorithm comprises any factor having an effect on the kinetics of the analyte-specific reaction.

31. System of claim 30, wherein the sample comprises whole blood and the factor is at least one of the interferents selected from the group consisting of sample temperature and hematocrit.

32. An evaluation instrument for use with an analysis element having at least two electrodes and an analyte reagent, the instrument comprising electronic circuitry configured to apply an analysis voltage to the electrodes relatively immediately after a sample is detected at the electrodes, and to measure a plurality of current values over time resulting from the application of the analysis voltage, up to at least the time at which a maximum current value is measured, and to use the plurality of values in an algorithm for interferent error compensation.

33. The instrument of claim 32, wherein the electronic circuitry is further configured to apply an AC-voltage to the electrodes generally simultaneously with application of the analysis voltage and to measure resulting AC current over substantially the same time, the measured AC current being used in the evaluation algorithm.

34. The instrument of claim 32, wherein the interferent for which the error compensation is made by the evaluation algorithm comprises any factor having an effect on the kinetics of the analyte-specific reaction.

35. System of claim 34, wherein the sample comprises whole blood and the factor is at least one of the interferents selected from the group consisting of sample temperature and hematocrit.

36. A method for the electrochemical determination of an analyte concentration in a sample, the sample forming a reaction layer by at least partially hydrating an analyte reactant, comprising the steps of applying an analysis voltage to the reaction layer, measuring over time a plurality of values of an analyte detection current resulting from the analysis voltage, identifying a maximum current value measured during the measuring step, terminating the measuring step relatively immediately after the identifying step, and deriving the analyte concentration by means of an evaluation algorithm comprising use of said plurality of values of the analyte detection current, the evaluation algorithm including compensation for interferent error.

37. The method of claim 36, further comprising the steps of applying an AC voltage to the reaction layer generally simultaneously with the step of applying an analysis voltage, and measuring the resulting AC-current generally simultaneously with the step of measuring the plurality of values of the analyte detection current for use in the evaluation algorithm.

38. The method of claim 36 or claim 37, wherein the terminating step occurs between about 5 and about 10 seconds after the analysis voltage applying step.

39. The method of claim 36 or claim 37, wherein the terminating step occurs between about 0.5 and about 5 seconds after the analysis voltage applying step.

40. The method of claim 36 or claim 37, wherein the terminating step occurs no more than about 0.5 seconds after the analysis voltage applying step.

41. The method of claim 36 or claim 37, wherein the interferent for which the error compensation is made by the evaluation algorithm comprises any factor having an effect on the kinetics of an analyte-specific reaction between the analyte and the analyte reactant in the reaction layer.

42. System of claim 36 or claim 37, wherein the sample comprises whole blood and the interferent for which the error compensation is made by the evaluation algorithm is at least one of the interferents selected from the group consisting of sample temperature and hematocrit.

43. An evaluation instrument for the electrochemical determination of an analyte concentration in a sample, the instrument comprising an electronic circuitry configured to adapt the time required for obtaining measurement results to be relative to the approximate time at which a maximum current value is measured in a reaction layer in electrical connection with the electronic circuitry, the reaction layer comprising an analyte reactant at least partially hydrated by the sample and having an analysis voltage applied thereto by the instrument relatively immediately after the reaction layer is detected by the instrument.

44. The system of claim 43, the instrument further configured to compensate for interferent error.

45. The system of claim 44, wherein the sample comprises whole blood, the interferent error being caused by at least one of the sample temperature and hematocrit.

46. The system of claim 43, wherein the time of the maximum current value is between about 0.5 and about 10 seconds.

* * * * *

UNITED STATES PATENT AND TRADEMARK OFFICE
CERTIFICATE OF CORRECTION

PATENT NO. : 7,638,033 B2
APPLICATION NO. : 11/246381
DATED : December 29, 2009
INVENTOR(S) : Kasielke et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1118 days.

Signed and Sealed this

Ninth Day of November, 2010

David J. Kappos
*Director of the United States Patent and Trademark Office*